United States Patent [19]

Pujado

[11] 4,333,801
[45] Jun. 8, 1982

[54] RECOVERY OF A CUMENE/ALPHA-METHYLSTYRENE FRACTION FROM A MIXTURE THEREOF WITH PHENOL AND WATER

[75] Inventor: Peter R. Pujado, Palatine, Ill.

[73] Assignee: UOP Inc., Des Plaines, Ill.

[21] Appl. No.: 289,591

[22] Filed: Aug. 3, 1981

[51] Int. Cl.³ ............................................... B01D 3/14
[52] U.S. Cl. ....................................... 203/94; 203/98; 203/DIG. 19; 568/749
[58] Field of Search .................... 203/DIG. 19, 94, 98; 585/800; 208/347, 350, 358; 568/810, 749

[56] References Cited

U.S. PATENT DOCUMENTS

| | | | |
|---|---|---|---|
| 2,728,795 | 12/1955 | Armstrong et al. | 568/810 |
| 2,824,048 | 2/1958 | Hupe et al. | 568/749 |
| 3,215,745 | 11/1965 | Frank | 568/810 |

Primary Examiner—Frank Sever
Attorney, Agent, or Firm—James R. Hoatson, Jr.; Robert W. Welch; William H. Page, II

[57] ABSTRACT

A process is disclosed for the recovery of a cumene/alpha-methylstyrene fraction from a mixture thereof with phenol and water. Said mixture is introduced into a fractionation column at conditions to separate an overhead fraction comprising cumene and alpha-methylstyrene and a phenol bottoms fraction. A vapor stream comprising cumene, alpha-methylstyrene and a phenol-water azeotrope is withdrawn from an intermediate level of said column and condensed to form an organic phase and an aqueous phase comprising phenol. The latter is discharged, and the former is recycled to the column. The overhead fraction thus requires substantially less caustic to neutralize the residual phenol container therein.

4 Claims, 1 Drawing Figure

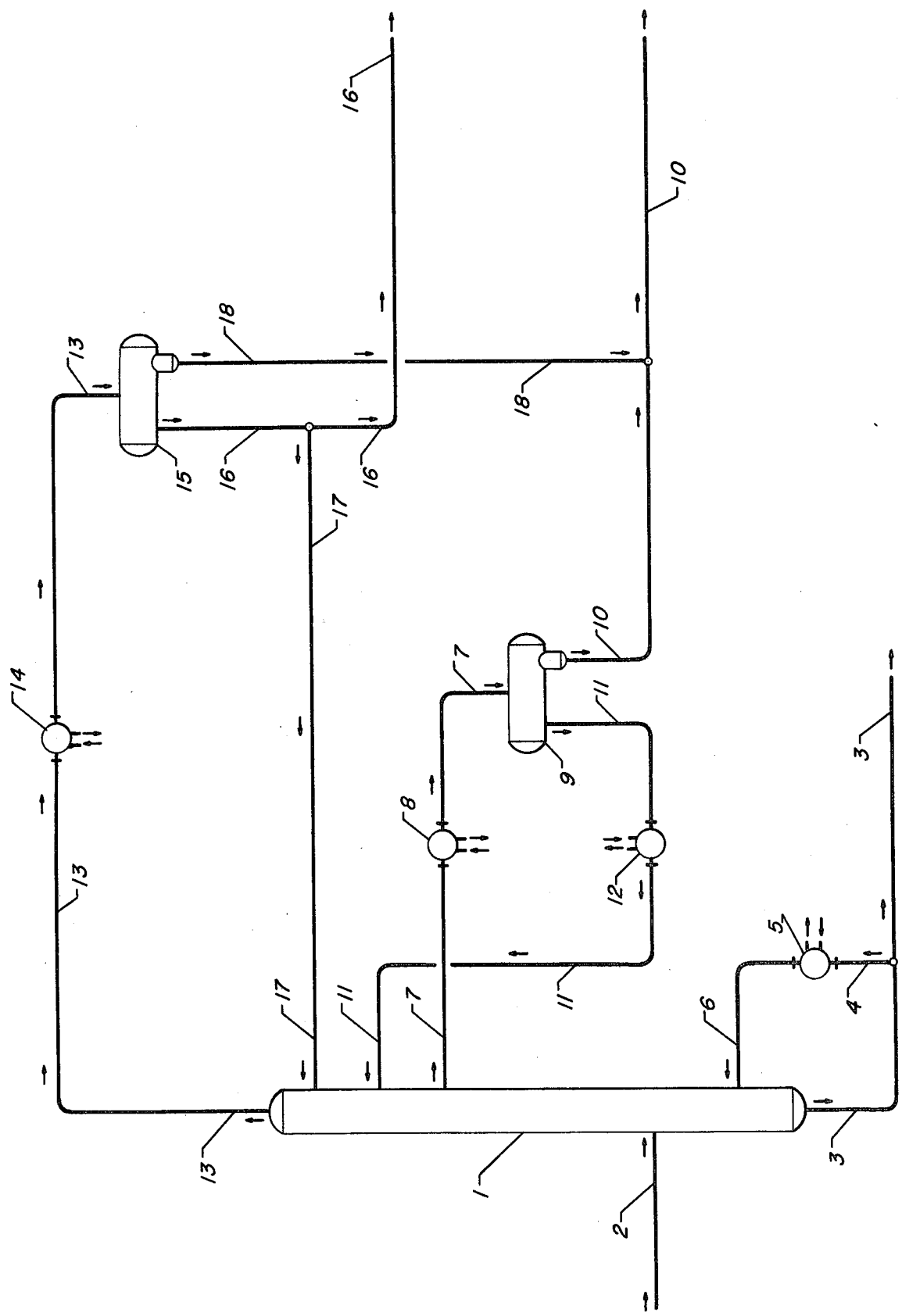

RECOVERY OF A CUMENE/ALPHA-METHYLSTYRENE FRACTION FROM A MIXTURE THEREOF WITH PHENOL AND WATER

This invention relates to the manufacture of phenols by the acid cleavage of an alpha-hydroperoxy derivative of an alkyl-substituted aromatic hydrocarbon. In particular, this invention relates to the manufacture of phenol by the acid cleavage of cumene hydroperoxide.

In general, phenols are prepared by the oxidation of an alkyl-substituted aromatic hydrocarbon, preferably a secondary alkyl-substituted aromatic hydrocarbon, followed by the acid cleavage of the resulting alpha-hydroperoxy derivative thereof. The acid cleavage is typically effected by means of an aqueous acid, usually a 50–98% aqueous sulfuric acid solution, although at least a 70% solution is preferred. Other suitable aqueous acids include aqueous hydrochloric or perchloric acid solutions. The acid cleavage reaction mixture will include a phenol, a ketone, water and unreacted alkyl-substituted aromatic hydrocarbons. The present invention is particularly directed to a process wherein phenol is prepared by the air oxidation of cumene, and by the subsequent sulfuric acid cleavage of the resulting cumene hydroperoxide. In addition to the principal products of phenol and acetone, the acid cleavage reaction mixture will further contain varying amounts of by-products, principally alpha-methylstyrene, as well as unreacted cumene.

In the process of recovering phenol from the acid cleavage reaction mixture, the reaction mixture is initially neutralized, either directly by the addition of caustic or indirectly by contact with an ion-exchange resin. In any case, the neutralized reaction mixture is fed to a distillation column, commonly referred to as a crude acetone column, at conditions to effect a crude separation of those materials boiling below phenol whereby an overhead fraction is recovered comprising substantially all of the acetone and lower boiling by-products as well as a substantial portion of the water and unreacted cumene. Acetone is subsequently recovered, as is the cumene, by further distillation of the crude acetone column overhead, the cumene being recycled to the oxidation phase of the process.

The bottoms fraction recovered from the crude acetone column, comprising phenol and alpha-methylstyrene as well as the balance of the water and unreacted cumene, is typically treated for the separation of heavy ends and thereafter fed to a distillation column, commonly referred to as a cumene column. The last mentioned column is operated at conditions to separate an overhead fraction comprising water, cumene and alpha-methylstyrene from the higher boiling phenol product. The phenol, recovered as the bottoms fraction, further contains certain impurities, e.g., mesityl oxide, hydroxy acetone, and the like, and said impurities are separated from the phenol product on further distillation.

The overhead fraction recovered from the cumene column will invariably comprise an azeotropic mixture of phenol and water admixed with the alpha-methylstyrene and unreacted cumene. While the alpha-methylstyrene can be separated and recovered as a useful by-product, it is more frequently subjected to hydrogenation and reduced to cumene in admixture with the unreacted cumene for recycle to the aforementioned oxidation step of the process. A significant amount of phenol is recovered in the overhead fraction from the cumene column, principally as a phenol-water azeotrope difficult to remove by simple distillation. Since phenol is well known as a powerful oxidation inhibitor, substantially all of the phenol must be separated from the cumene prior to recycle to the oxidation phase of the process. This has heretofore been accomplished by subjecting the overhead fraction from the cumene column to a caustic wash involving a considerable volume of caustic.

It is an object of this invention to present an improved method for the separation of cumene and alpha-methylstyrene from a mixture thereof with phenol whereby the cumene/alpha-methylstyrene is recovered substantially reduced in phenol and requiring minimal caustic wash.

In one of its broad aspects, the present invention embodies a process for the recovery of a fraction comprising a secondary alkylbenzene and the corresponding secondary monoalkenylbenzene from a mixture thereof with a phenol and water which comprises the steps of (a) introducing said mixture into a fractionation column at an intermediate level, said column being operated at conditions to separate an overhead fraction comprising said secondary alkylbenzene and said secondary monoalkenylbenzene, and a bottoms fraction comprising said phenol; (b) recovering one portion of said overhead fraction, and returning another portion thereof as reflux to said column; (c) withdrawing a vapor stream from a level in said column above the aforementioned intermediate level, said vapor stream comprising at least a portion of said secondary alkylbenzene and said secondary alkenylbenzene and an azeotropic mixture of said phenol and water; (d) condensing said vapor stream and forming an organic phase and an aqueous phase comprising said phenol; and, (e) discharging said aqueous phase, and recycling said organic phase to said column at a level above that at which said vapor stream is withdrawn and below that at which said secondary alkylbenzene/secondary alkenylbenzene fraction is returned to said column as reflux, said organic phase being recycled to said column at conditions to maintain vapor phase conditions therein.

One of the more specific embodiments concerns a process for the recovery of a cumene/alpha-methylstyrene fraction from a mixture thereof with phenol and water which comprises the steps of (a) introducing said mixture into a fractionation column at an intermediate level, said column being operated at conditions including a bottoms temperature of from about 160° to about 180° C. and a top temperature of from about 90° to about 105° C. to separate an overhead fraction comprising cumene and alpha-methylstyrene and a bottoms fraction comprising phenol; (b) recovering one portion of said overhead fraction, and returning another portion thereof as reflux to said column; (c) withdrawing a vapor stream from a level in said column above the aforementioned intermediate level, said vapor stream comprising cumene, alpha-methylstyrene and an azeotropic mixture of phenol and water; (d) condensing said vapor stream and forming an organic phase comprising cumene and alpha-methylstyrene and an aqueous phase comprising phenol; (e) discharging said aqueous phase, and recycling said organic phase to said column at a level about that at which said cumene/alpha-methylstyrene fraction is returned to said column as reflux, said organic phase being recycled to said column at a temperature of from about 160° to about 180° C. to maintain vapor phase conditions therein.

Other objects and embodiments of this invention will become apparent in the following detailed specification.

The overall process to which this invention pertains concerns the oxidation of an alkyl-substituted aromatic hydrocarbon, and the alpha hydroxy derivatives thereof may be represented by the general formula

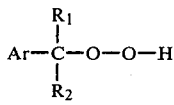

wherein Ar represents an aromatic hydrocarbon radical which may be an aryl radical or an alkaryl radical, and the hydroperoxy group (—O—O—H) is attached to a carbon atom alpha the aromatic nucleus, and $R_1$ and $R_2$ may be hydrogen or the same or different alkyl, cycloalkyl, aryl, aralkyl or alkaryl hydrocarbon radicals, or $R_1$ and $R_2$ together with the said alpha carbon atom to which they are attached may form a cycloalkyl group containing up to about 8 carbon atoms, for example, as in the case of 1-phenyl-1-hydroperoxy-cyclohexane. $R_1$ and $R_2$ are preferably n-alkyl hydrocarbon radicals so that the hydroperoxide is an alpha hydroperoxy derivative of a secondary alkylbenzene. The alpha hydroperoxy derivatives of alkyl substituted aromatic hydrocarbons herein contemplated thus include benzyl hydroperoxide, alpha-methylbenzyl hydroperoxide, alpha-methyl-p-methylbenzyl hydroperoxide, alpha,alpha-dimethylbenzyl hydroperoxide (cumene hydroperoxide), alpha,alpha-dimethyl-p-methylbenzyl hydroperoxide, alpha,alpha-dimethyl-p-ethylbenzyl hydroperoxide, alpha,alpha,alpha,alpha'-tetramethyl-p-xylyl dihydroperoxide, alpha-methyl-alpha-phenylbenzyl hydroperoxide, alpha-alpha-dimethylnaphthylmethyl hydroperoxide, 1, phenylcyclohexyl hydroperoxide, and the like. The present invention is particularly directed to a process for the recovery of phenol from a reaction mixture resulting from the acid cleavage of alpha, alpha-dimethylbenzyl hydroperoxide, or isopropylbenzene hydroperoxide, more commonly referred to as cumene hydroperoxide.

The aforesaid oxidation reaction is effected at conditions well known in the art. The hydroperoxide oxidation product can be prepared by direct liquid phase oxidation of the selected alkyl-substituted aromatic hydrocarbon with oxygen, or an oxygen-containing gas such as air, usually at an elevated temperature. The oxidation reaction proceeds slowly through an initial induction period, accelerating to a more favorable rate with the formation of the hydroperoxide which exerts a catalytic effect on the oxidation reaction. This initial induction period is eliminated, or substantially reduced, by initially including a hydroperoxide in the reaction mixture, usually the hydroperoxide product of the reaction. However, other materials are disclosed in the art which exhibit a similar catalytic effect. Temperatures effecting the oxidation reaction range from about room temperature to about the boiling point of the hydrocarbon subjected to oxidation, which, in the case of cumene, is about 305° F. In general, it is preferred to utilize an elevated temperature in the range of from about 120° to about 265° F. The optimum temperature will depend on the particular alkyl-substituted aromatic hydrocarbon to be oxidized and on the reaction conditions otherwise employed. The oxidation can be effected at pressures ranging from about atmospheric to about 500 psig, although a pressure not exceeding about 90 psig is generally preferred. It is desirable to limit the contact time of the reactants at oxidation conditions to effect substantially less than complete conversion of the alkyl-substituted aromatic hydrocarbon to the corresponding hydroperoxide. For example, in the oxidation of cumene, it is desirable to limit the contact time of the cumene and the oxidizing agent so that the concentration of the resulting cumene hydroperoxide does not exceed about 30 wt.%.

As heretofore mentioned, acid cleavage of the cumene hydroperoxide is preferably effected utilizing at least about a 70% aqueous sulfuric acid solution, and the acid cleavage reaction mixture is subsequently neutralized either indirectly, for example, by the addition of caustic or directly, for example, on contact with an ion exchange resin. In any case, the neutralized reaction mixture is charged to the crude acetone column which is operated at conditions to effect a crude separation of those materials boiling below phenol. The crude acetone column is typically operated at a top pressure of from about 10 to about 15 psig and a bottom pressure of from about 15 to about 25 psig, and at a top temperature of from about 70° to about 80° C. and a bottom temperature of from about 165° to about 175° C. whereby an overhead fraction is recovered comprising substantially all of the acetone and lower boiling by-products as well as a substantial portion of the water and unreacted cumene. The bottoms fraction, which is the subject of this invention, is treated for the separation of heavy ends by conventional means, and thereafter for the recovery of cumene and alpha-methylstyrene substantially free of phenol in accordance with the process of the present invention. Said bottoms fraction will comprise phenol and alpha-methylstyrene as well as the balance of the water and unreacted cumene.

The further description of the process of this invention is presented with reference to the attached drawing.

The drawing is a simplified flow diagram of a cumene column modified to accommodate the process of this invention and representing one preferred embodiment thereof. The drawing is not intended as an undue limitation on the generally broad scope of the invention as set out in the appended claims. Certain hardware such as valves, pumps, compressors, heat exchangers, instrumentation and controls have been omitted as not essential to a clear understanding of the invention, the use and application of such hardware being well within the skill of the art.

Referring then to the drawing, a bottoms fraction from a crude acetone column, not shown, is charged to a cumene column 1 at an intermediate level by way of line 2. Said bottoms fraction comprises about 129 moles of phenol, 29 moles of cumene, 5 moles of alpha-methylstyrene and 38 moles of water charged to said cumene column on an hourly basis. A phenol fraction is withdrawn from the bottom of the column via line 3 and a portion thereof is diverted to line 4 to be reheated in a heating means 5 and returned to the column through line 6 to maintain the bottom temperature of from about 160° to about 180° C. The balance of the phenol fraction is continued through line 3 at a rate of about 129 moles per hour, and this stream is further treated in distillation means, not shown, for the recovery of a substantially pure phenol product.

A vaporous sidecut, comprising cumene, alpha-methylstyrene, and an azeotropic mixture of phenol and water, is taken from the cumene column 1 at a level above that at which the aforesaid crude acetone bottoms fraction is introduced, the vapor stream being withdrawn through line 7 and a condensing means 8. The resulting condensate is collected in a settler 9 wherein an aqueous phase is allowed to settle out from an organic phase comprising cumene and alpha-methylstyrene. The aqueous phase is discharged from the settler 9 into line 10, about 0.2 moles of phenol and 38 moles of water per hour being separated in this manner.

The upper organic phase recovered from the settler 9 is saturated with water and contains an amount of phenol corresponding to that given by the partition coefficient of phenol between the organic phase and the aqueous phase. This organic phase is then reheated in a heating means 12 located in line 11 and reintroduced into the cumene column 1 at a temperature of from about 160° to about 180° C. and in a substantially vaporous state. Alternatively, this organic phase may be recycled as a liquid except that in this case, a higher reboiler heat duty or use of an intermediate reboiler may be required. The organic phase from the settler 9 is reintroduced into the cumene column 1 at a level above that at which the first mentioned vapor stream is withdrawn and below that at which the hereinafter described overhead fraction is returned to said column as reflux.

Cumene and alpha-methylstyrene are recovered from the cumene column 1 as an overhead fraction containing less than about 300 mole ppm phenol. This overhead fraction is withdrawn via line 13 and passed through a condensing means 14 to an overhead receiver 15. Cumene and alpha-methylstyrene are recovered from the receiver 15 by way of line 16, and one portion is diverted to the top of the cumene column 1 via line 17 to establish a reflux ratio therein of from about 1.6 to about 2. The remaining portion of the cumene/alpha-methylstyrene fraction is continued through line 16 to a caustic scrubber, not shown. Line 18 is provided to discharge any water accumulation in the overhead receiver 15, said water being discharged into line 10 to be subsequently treated for the recovery of phenol in admixture with the water/phenol mixture passing therethrough.

The process practiced herein requires substantially less caustic to neutralize the residual phenol contained in the cumene/alpha-methylstyrene fraction than has heretofore been the case. This results not only in a savings in caustic but also in a substantial alleviation of the caustic disposal problem. In addition, it accomplishes the substantial removal of most of the phenol from the overhead cumene/alpha-methylstyrene fraction in a single column in an operation which would otherwise normally require two columns. This results in a reduction in capital investments costs for the construction of these units.

I claim as my invention:

1. A process for the recovery of a fraction comprising a secondary alkylbenzene and the corresponding secondary monoalkenylbenzene from a mixture thereof with a phenol and water which comprises the steps of:
(a) introducing said mixture into a fractionation column at an intermediate level, said column being operated at conditions to separate an overhead fraction comprising said secondary alkylbenzene and said secondary monoalkenylbenzene, and a bottoms fraction comprising said phenol;
(b) recovering one portion of said overhead fraction, and returning another portion thereof as reflux to said column;
(c) withdrawing a vapor stream from a level in said column above the aforementioned intermediate level and below the withdrawl point of said overhead fraction, said vapor stream comprising at least a portion of said secondary alkylbenzene and said secondary alkenylbenzene and an azeotropic mixture of said phenol and water;
(d) condensing said vapor stream and forming an organic phase and an aqueous phase; and,
(e) discharging said aqueous phase, and recycling said organic phase to said column at a level above that at which said vapor stream is withdrawn and below that at which said secondary alkylbenzene/secondary alkenylbenzene fraction is returned to said column as reflux, said organic phase being recycled to said column at conditions to maintain the vapor phase conditions therein.

2. The process of claim 1 further characterized in that said secondary alkylbenzene is cumene and said corresponding secondary monoalkenylbenzene is alpha-methylstyrene.

3. The process of claim 2 further characterized with respect to step (a) in that said conditions include a bottom temperature of from about 160° to about 180° C. and a top temperature of from about 90° to about 105° C.

4. The process of claim 2 further characterized with respect to step (e) in that said conditions include a temperature of from about 160° to about 180° C.

* * * * *